United States Patent
Sabczynski et al.

(10) Patent No.: US 6,739,752 B2
(45) Date of Patent: May 25, 2004

(54) METHOD AND DEVICE FOR CALIBRATING A GRAVITY-SENSITIVE IMAGE PICK-UP DEVICE AND FOR IMAGING BY MEANS OF SUCH AN IMAGE PICK-UP DEVICE

(75) Inventors: Joerg Sabczynski, Norderstedt (DE); Waldemar Zylka, Herten (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 37 days.

(21) Appl. No.: 10/294,293

(22) Filed: Nov. 14, 2002

(65) Prior Publication Data

US 2003/0095637 A1 May 22, 2003

(30) Foreign Application Priority Data

Nov. 16, 2001 (DE) .......................... 101 56 445

(51) Int. Cl.[7] .............................................. G01D 18/00
(52) U.S. Cl. ..................... 378/207; 378/189; 378/193
(58) Field of Search ................. 378/207, 189, 378/193

(56) References Cited

U.S. PATENT DOCUMENTS 5,748,768 A * 5/1998 Sivers et al. ............... 382/130
5,774,519 A * 6/1998 Lindstrom et al. ............ 378/18
6,285,902 B1   9/2001 Kienzle

OTHER PUBLICATIONS

Kelly, Alonzo; "Introduction to Mobile Robots, Position Estimation 3: Sensors for Position Estimation"; Gefunden im Internet:www.frc.ri.cmu.edu, 1996.

* cited by examiner

Primary Examiner—Craig E. Church
Assistant Examiner—Jurie Yun
(74) Attorney, Agent, or Firm—Thomas M. Lundin, Esq.

(57) ABSTRACT

A description is given of a method and a device for the calibration of an image pick-up device which is sensitive to gravity. Also described are a method and a device for imaging by means of such an image pick-up device; they are used in particular in X-ray systems, for example, systems provided with a C-arm. Calibration is performed essentially by forming and storing a look-up table whereby the calibration data required for the correction of distortions due to the supporting construction is associated with a plurality of position data of the supporting construction. During imaging the direction of the force of gravity relative to the supporting construction is measured; therefrom the position data is calculated and the calibration data associated with this data in the table is read out and used for the correction of the acquired image.

10 Claims, 1 Drawing Sheet

METHOD AND DEVICE FOR CALIBRATING A GRAVITY-SENSITIVE IMAGE PICK-UP DEVICE AND FOR IMAGING BY MEANS OF SUCH AN IMAGE PICK-UP DEVICE

BACKGROUND

The invention relates to a method and a device for the calibration of an image pick-up device which is sensitive to gravity, for example, because of the fact that it is built into a projecting supporting construction, meaning that the image geometry can be influenced and notably image deformation can be induced by mechanical deformation of the supporting construction. The invention also relates to a method and a device for imaging by means of such an image pick-up device, notably as used in X-ray systems, for example, systems provided with a C-arm. Finally, the invention also relates to an X-ray system provided with such devices.

Image distortions of this kind occur notably in the case of projecting and movable mechanical supporting constructions for such imaging devices, that is, due to mechanical deformations. This problem is encountered notably in X-ray systems in which the image pick-up device is attached to an arm (C-arm) which is rotatable about a patient and at one end of which the image pick-up device is mounted whereas an X-ray source is situated at its other end. Because of the comparatively large dimensions of the arm and the comparatively large weight of these two components, the C-arm may be deformed to such a great and varying extent, depending on its rotary position, that the acquired images are distorted.

WO 00/66971 discloses a device for the measurement of the position and orientation of a body while utilizing means for determining the direction of the gravity vector, as well as a method of correcting X-ray images which have been distorted by the force of gravity and the terrestrial magnetic field. In order to correct an acquired and digitized X-ray image, first the direction of the gravity vector and the position and orientation of the X-ray apparatus are measured and subsequently the distortions of the X-ray image as caused by the deformation of the X-ray apparatus and by the local terrestrial magnetic field are determined and ultimately these distortions in the stored X-ray image are corrected by means of a computer. A significant drawback, however, is then encountered in that the image correction necessitates the presence of the device for determining the exact position and orientation of the X-ray apparatus as well as possibly an additional computer. This additional hardware is disadvantageous notably in the case of mobile X-ray apparatus.

SUMMARY OF THE INVENTION

Therefore, it is an object of the invention to provide a method and a device which enable comparatively simple and reliable calibration of an image pickup device in respect of image distortions of the kind set forth.

One object of the invention to provide a method and a device for calibration which is suitable notably for use in C-arm X-ray systems in order to compensate for image distortions which are caused by the mechanical deformations of the C-arm which are due to the force of gravity.

Another object of the invention to provide a method and a device for imaging which is conceived notably for use in conjunction with an image pick-up device calibrated in accordance with the invention and is optionally conceived also for surgical navigation.

Yet another object of the invention to provide an X-ray system which is notably suitable for mobile applications and in which the described gravitational effects can be compensated for without requiring a significant amount of additional hardware such as, for example, a position measuring system. One skilled in the art will recognize that the principles of the invention may be accomplished by meeting one of the recited objects, any combination of the recited objects or non-recited advantages and/or objects that will become apparent to one skilled in the art upon understanding the specification, claims and drawings disclosed herein.

Objects in accordance with accordance with principles of the invention are achieved with a method including the calibration of an image pick-up device which is mounted on a gravity-sensitive supporting construction, the method comprises determining calibration data (calibration base points) in a plurality of selected positions of the supporting construction, which calibration data is suitable for distortion correction of the image acquired by the image pick-up device in the relevant position; determining position data of the supporting construction in the selected positions, said position data being related each time to the direction of the force of gravity, and associating the position data with the calibration data in a lookup table.

An apparatus in accordance with principles of the present invention comprises a device for determining the direction of the force of gravity relative to a position of the supporting construction, and an arithmetic and storage unit for determining position data, related to the direction of the force of gravity, for a plurality of selected positions of the supporting construction and for forming and storing a look-up table whereby the position data is associated with the respective calibration data suitable for the removal of image distortions caused by mechanical deformations in the respective positions.

Objects of the present invention may also be achieved in conformity with a method of imaging by means of an image pick-up device which is attached to a gravity-sensitive supporting construction, the method comprising acquiring an image of an object to be examined in a selected position of the supporting construction, determining position data, related to the direction of the force of gravity, of the supporting construction in the selected position, comparing the position data determined with the position data stored in a look-up table, reading out calibration data stored in the look-up table at position data which correspond at least essentially to the position data determined, and removing the distortions from the acquired image by means of the calibration data read out.

Another apparatus in conformity with aspects of the present invention is a device for carrying out the image forming method, the device comprises a means for determining the direction of the force of gravity relative to the supporting construction, an arithmetic and storage unit for determining position data, related to the direction of the force of gravity, of the supporting construction in order to compare this position data with the position data stored in a look-up table, for reading out calibration data stored at position data in the look-up table which correspond at least essentially to the position data determined, and for removing the distortions from the acquired image of the object to be examined or for distorting the image of an instrument introduced into the object to be examined, by way of the read out and possibly interpolated calibration data, and a display unit for displaying the distortion-corrected image of the object to be examined or for displaying the distorted image of the object to be examined in which the distorted image of the instrument is reproduced.

Advantages of these solutions consist first of all in that essentially higher image qualities can thus be achieved in a controlled manner, that they can be easily carried out and that they are also suitable for use in conjunction with mobile X-ray systems, without the customary position measuring systems being required.

It is also possible to correct distortions which arise due to a curved surface of the entrance window of the image intensifier.

Further advantageous embodiments of a devices in accordance with principles of the present invention include, in one case the calibration data can be calculated by means of a phantom object or, using another approach, by means of a physical model of the mechanical deformation of the supporting construction.

Another embodiment in conformity with aspects of the present invention is particularly suitable in the case of having position data that represents the pivoting angle supporting constructions.

Yet another embodiment in conformity with aspects of the present invention, that is suitable in particular for surgical navigation, includes a method for imaging comprising acquiring an image of an object to be examined in a selected position of the supporting construction and determining position data, related to the direction of the force of gravity, of the supporting construction in the selected position. The method includes comparing the position data determined with the position data stored in a look-up table and reading out calibration data stored in the look-up table at position data which corresponds at least essentially to the position data determined. The method further comprises determining the position and acquiring a (virtual) image of an instrument introduced into the object to be examined, calculating a virtual, distorted image of the instrument, introduced into the object to be examined, by means of the calibration data read out, and reproducing the distorted image of the introduced instrument in the acquired image of the object to be examined.

The following description, claims and accompanying drawings set forth certain illustrative embodiments applying various principles of the present invention. It is to be appreciated that different embodiments applying principles of the invention may take form in various components, steps and arrangements of components and steps. These described embodiments being indicative of but a few of the various ways in which some or all of the principles of the invention may be employed in a method or apparatus. The drawings are only for the purpose of illustrating an embodiment of an apparatus and method applying principles of the present invention and are not to be construed as limiting the present invention.

BRIEF DESCRIPTION OF THE DRAWINGS

The foregoing and other features and advantages of the present invention will become apparent to those skilled in the art to which the present invention relates upon consideration of the following detailed description of apparatus applying aspects of the present invention with reference to the accompanying drawings, wherein.

DETAILED DESCRIPTION

Figure 1:
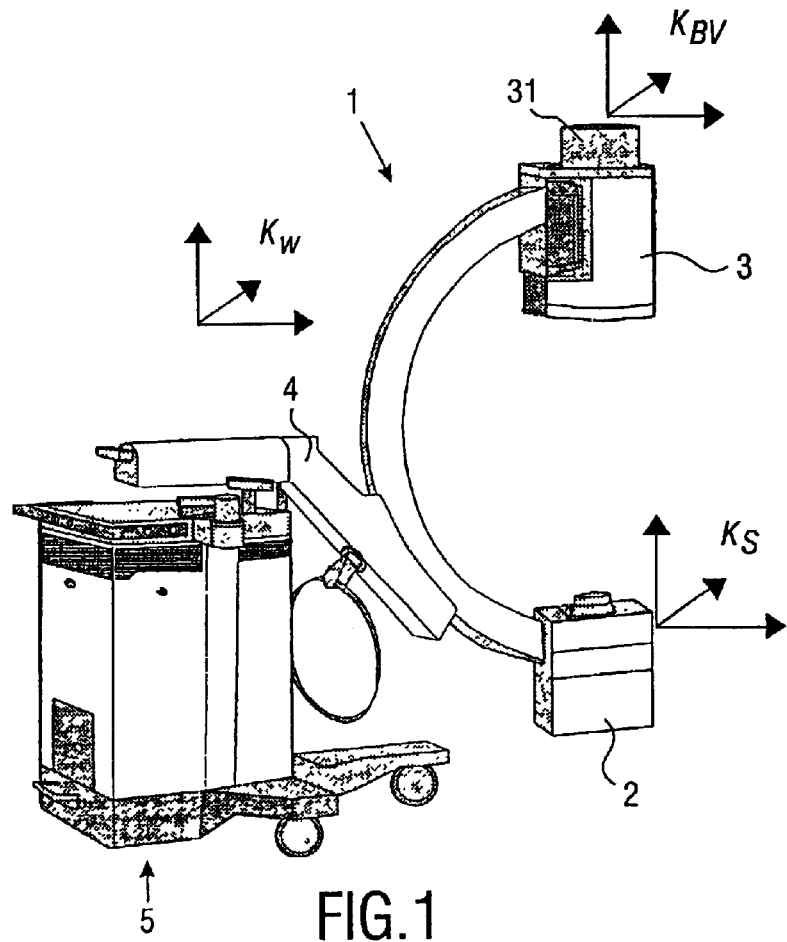
FIG. 1 is a diagrammatic overall view of an X-ray system provided with a device in accordance with the invention.

FIG. 1 shows a mobile X-ray system which includes a C-arm 1, at one end of which there is mounted an X-ray source 2 while an X-ray detector 3 with an image intensifier is mounted at the other end thereof. Moreover, a triaxial acceleration meter 31 which measures the direction of the gravitational field relative to the C-arm 1 is also mounted on the C-arm 1. The C-arm 1 is mounted so as to be pivoted on a mount 4 which itself is attached to a table 5. The table 5 is displaceable and provided with control elements and supply and operating devices for the X-ray system.

An object to be examined (a patient) is positioned between the source 2 and the detector 3; generally speaking, the C-arm 1 on the mount 4 can then be pivoted through an angle of at least 180° so as to enable optimum irradiation of the zone to be examined.

As has already been stated, such a C-arm is liable to be deformed by the weight of the X-ray source 2, the X-ray detector 3 and the image intensifier, so that images picked up are distorted. Therefore, a calibration is to be performed so as to compensate for the deformations which are dependent on the pivoted position of the C-arm, thus correcting the different distortions caused thereby.

The calibration is performed after the manufacture of the X-ray system as well as possibly at regular intervals (service intervals). The essential steps of such a method will be described in detail hereinafter. However, modified versions of this method or other methods can alternatively be carried out.

Figure 2:
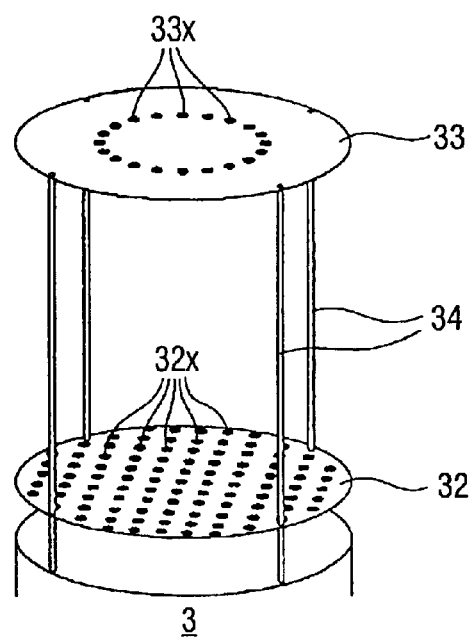
FIG. 2 is a diagrammatic representation of an arrangement for the calibration of the X-ray system.

First a phantom object in the form of two parallel plates 32, 33 is attached to the X-ray detector 3 as shown in FIG. 2. Bars 34 which are also suitable for keeping the plates in parallel are provided for this purpose. The first plate 32 is situated directly in front of the entrance window of the detector 3 and is provided with a plurality of circular surfaces or spheres 32x which are arranged at the grid points of an imaginary square grid and are impervious to X-rays. Between the first plate 32 and the X-ray source 2 there is arranged the second plate 33 which is situated at a distance of, for example, approximately 37 cm from the first plate. The second plate is provided with a plurality of equally large and also X-ray impervious circular surfaces or spheres 33x which, however, are arranged along the circumference of a centered circle.

The first plate 32 serves to determine the distortion parameters of a projection image whereas the second plate 33 serves to determine the actual focal point position, that is, each time for a plurality of selected pivoted positions of the C-arm 1. The distortion parameters and focal point positions determined are stored as distortion data sets for each of the pivoted positions of the C-arm 1.

More specifically, the circular surfaces or spheres 32x of the first plate 32 are projected onto the detector 3, are detected by means of a segmentation algorithm and associated with the individual circular surfaces or spheres 32x on the first plate whose positions are known. In conjunction with appropriate interpolation between the surfaces, the distortion parameters can thus be calculated in known manner for "each" X-ray beam and hence for each pixel.

Furthermore, the focal point position is calculated in known manner while using the image of the circle of circular surfaces 33x which is projected onto the detector by the second plate 33, and also while using the ratio of the diameter of this circle to that of the projected circle.

The distortion data sets acquired for each pivoted position of the C-arm 1 are then used to calculate calibration data (calibration base points) which are stored and are suitable for correcting the errors, caused by the distortions and focal point shifts, in an image acquired in the relevant pivoted position.

Furthermore, the triaxial acceleration meter 31 measures the direction of the gravitational field relative to the C-arm in each of the pivoted positions of the C-arm 1. Position data of the C-arm, notably its actual pivoted angle or its rotary position, in relation to said direction is calculated therefrom.

Finally, such position data is stored, together with the calibration data determined for this position, in an associated fashion in a look-up table.

The calibration of the X-ray system is terminated when calibration data and associated position data has been determined and stored in the look-up table for an adequate number of pivoted positions of the C-arm 1.

Alternatively, the look-up table could also be calculated on the basis of a physical model of the mechanical deformation of the C-arm in various positions as well as the calibration data each time required for the correction.

For the calibration, that is, for the formation and storage of the look-up table, either a separate arithmetic and storage unit is provided or the calibration is performed by means of an appropriate data processing program while utilizing an arithmetic unit already included in the relevant X-ray system.

For imaging during the examination of a patient or another object, the C-arm 1 is first rotated, as is customary, to a position in which the region of interest can be irradiated and a corresponding image can be projected onto the image intensifier. When this position is reached, the image is acquired in known manner. Furthermore, the triaxial acceleration meter 31 measures the gravitational field in respect of its direction relative to the C-arm. From this relative direction of the gravitational field the position data of the C-arm 1 is calculated and compared with the position data stored in the look-up table. When a corresponding or substantially corresponding entry is found, the calibration data associated with the relevant entry is read and used for correcting the acquired image in known manner.

Alternatively, the position data of the C-arm can also be calculated during the calibration and the imaging, for example, by means of an optical position measuring system (OPMS) so that the accelerationmeter is not necessary. Furthermore, the accelerationmeter could also be attached to a system which tracks the pivoted position of the C-arm in order to calculate the position data of the C-arm from this position.

If no adequate correspondence is found between the position data determined and the position data stored in the table, the relevant calibration data must be interpolated. To this end, the calibration data is considered as calibration base points. Various methods can be used in this respect. The application of an approximated Delauney triangulation will now be described by way of example.

This is an approximation of the triangulation, because the calibration base points are situated on a spherical surface, but the Delauney triangles formed by the base points are to be treated as planar triangles for the sake of simplicity. Therefore, prior to the interpolation each base point must be projected onto such planar triangles.

The original (planar) method is executed as follows. Let there be a set of calibration base points to be interpolated on a spherical surface. The triangulation algorithm leads to a set of non-intersecting planar triangles whose corners are formed by respective calibration base points, so that the entire surface is covered by triangles.

Any intermediate point P (that is, a calibration base point to be interpolated) can then be unambiguously associated with one of the triangles. The corner points of this triangle constitute the three calibration base points which are nearest to the point P. The base points to be selected for the interpolation are thus determined.

The Delauney triangulation is unambiguous. For a two-dimensional plane the algorithm is as follows: first all feasible triangles are formed from the set of calibration base points. The triangles whose corner points are collinear are not taken into account. When the circle circumscribing a triangle contains other base points, the triangle is not taken into account either. The triangle is used only in the absence of these two events.

However, because the calibration base points are actually situated on a spherical surface, in order to avoid geometrical distortions and other problems the Delauney triangulation is adapted to a spherical interpolation and modified (approximated) in such a manner that the calibration base points are transformed in a three-dimensional Cartesian co-ordinate system. For each triplet of coplanar base points the corresponding triangle is not taken into account.

Instead of the above circumscribed circle, an enclosing sphere is formed and the radius thereof is compared with the three-dimensional Euclidian distance from any other calibration base point. It can be demonstrated that this criterion is equivalent to the normal two-dimensional Delauney triangulation when the base points are situated on an ideal spherical surface. When the enclosing sphere contains other base points, the triangle is disregarded. The triangle can be used if this is not the case.

In order to simplify as well as to accelerate the interpolation calculations, instead of the point P on the spherical surface the projection P' of the point P onto the plane triangle surface is considered. This gives rise to minor distortion effects in the interpolation contributions, but only in the case of large triangles.

When the triangulation is terminated, the interpolation by the planar triangles can be simply calculated while utilizing barycentric co-ordinates. A point P' situated in the plane (C1, C2, C3) can be described by its barycentric co-ordinates (B1, B2, B3). Hereinafter it is assumed that a point P on the spherical surface for which the interpolation coefficients are to be calculated is projected on each planar triangle surface to be taken into account (point P').

The barycentric co-ordinates contain respective information concerning the relative position of the point P' in relation to one of the sides of the triangle. For a corner point C1 of the triangle B1 is negative when the point P' lies beyond the line extending through the corner points C2 and C3; it is zero when it lies on this line and positive when it is situated at the same side of the line as the corner point C1.

The barycentric co-ordinates thus constitute a simple criterion for the localizing of the appropriate interpolation triangle. The point P' is situated within the triangle only if all values Bi are larger than 0.

After determination of the barycentric co-ordinates in this manner, the values to be interpolated for the point P' can be determined by way of a simple linear combination, enabling the interpolated calibration base point to be calculated so as to correct the acquired image.

For the imaging, and also for a possibly necessary interpolation, there is provided either a separate arithmetic and storage unit or a corresponding data processing program which is executed by means of an arithmetic unit already present in the relevant X-ray system.

It is also to be noted that the principle of the invention can be employed not only for distortion correction of an acquired image, but also, for example, for surgical navigation. In that case it is not of prime importance to correct an acquired image for distortions, but to determine as accurately as possible the position of an instrument (for example, a catheter) introduced into the patient and to superpose this position on the acquired image by means of an appropriate image processing system.

On the one hand an X-ray image of the zone of a patient to be examined is then acquired in a conventional manner, without this image being corrected for distortion. On the other hand, the instantaneous position of the introduced instrument is continuously determined by means of a known method or a position measuring apparatus (for example, by means of a small transmitter or an inductance at the tip of the instrument). This position is then distorted by (reverse) application of the look-up table describing the distortion properties of the X-ray apparatus. In other words, this means that the (virtual) image of the introduced instrument is distorted in conformity with the imaging properties of the X-ray apparatus which are stored in the form of the calibration data. This distorted image is reproduced, while using an appropriate display unit, in the acquired (distorted) X-ray image, so that the instrument appears in the X-ray image in the correct position.

This offers the advantage that only one X-ray image need be formed even in the case of continuous tracking or continuously updated reproduction of the (usually guided) instrument. Moreover, the instrument need not have been introduced yet when this image is formed, so that the X-ray image cannot be affected thereby either.

Distortion correction of the image is not necessary, because only the actual position of the instrument relative to the object to be examined is of importance.

The invention is of course not limited to the described or shown embodiments, but generally extends to any embodiment, which falls within the scope of the appended claims as seen in light of the foregoing description and drawings. While a particular feature of the invention may have been described above with respect to only one of the illustrated embodiments, such features may be combined with one or more other features of other embodiments, as may be desired and advantageous for any given particular application. From the above description of the invention, those skilled in the art will perceive improvements, changes and modification. Such improvements, changes and modification within the skill of the art are intended to be covered by the appended claims.

Having described a preferred embodiment of the invention, the following is claimed:

1. A method for calibration of an image pick-up device which is mounted on a gravity-sensitive supporting construction, the method comprising:
   determining calibration data in a plurality of selected positions of the supporting construction, the determined calibration data suitable for distortion correction of an image acquired by an image pick-up device in the relevant position;
   determining position data of the supporting construction in the selected positions, the data being related each time to the direction of the force of gravity; and
   associating the position data with the calibration data in a look-up table.

2. The method of claim 1 wherein the calibration data is acquired by means of a phantom object.

3. The method of claim 1 wherein the calibration data is calculated by means of a physical model of the mechanical deformation of the supporting construction.

4. The method of claim 1 wherein the position data represents the pivoting angle of the supporting construction.

5. A device for calibration of an image pick-up device which is mounted on a gravity-sensitive supporting construction, the device comprising:
   means for determining the direction of the force of gravity relative to a selected position of the supporting construction; and
   an arithmetic and storage unit for determining position data, related to the direction of the force of gravity, for a plurality of selected positions of the supporting construction and for forming and storing a look-up table whereby the position data is associated with respective calibration data which is suitable for the removal of image distortions caused by mechanical deformations in these positions.

6. A method for imaging by means of an image pick-up device which is attached to a gravity-sensitive supporting construction, the method comprising:
   determining calibration data of an image pick-up device;
   acquiring an image of an object to be examined in a selected position of the supporting construction;
   determining position data, related to the direction of the force of gravity, of the supporting construction in the selected position;
   comparing the determined position data with position data stored in a look-up table;
   reading out calibration data stored in the look-up table at position data which corresponds at least essentially to the determined position data; and
   removing the distortions from the acquired image by means of the calibration data read out.

7. A method for imaging by means of an image pick-up device attached to a gravity-sensitive supporting construction, the method comprising:
   determining calibration data of an image pick-up device;
   acquiring an image of an object to be examined in a selected position of the supporting construction;
   determining position data, related to the direction of the force of gravity, of the supporting construction in the selected position;
   comparing the determined position data with position data stored in a look-up table;
   reading out calibration data stored in the look-up table at position data which corresponds at least essentially to the determined position data;
   determining the position and acquiring a virtual image of an instrument introduced into the object to be examined;
   calculating a virtual, distorted image of the instrument, introduced into the object to be examined, by means of the calibration data read out; and
   reproducing the distorted image of the introduced instrument in the acquired image of the object to be examined.

8. A computer usable media which includes program code instructions for controlling a general purpose digital computer in performing a desired function comprising:
   a determining process for providing calibration data in a plurality of selected positions of a supporting construction of an imaging system, the determined calibration data suitable for distortion correction of an image acquired by an image pick-up device of the imaging system in the relevant position;

a determining process for providing position data of the supporting construction in the selected positions, the position data being related each time to the direction of the force of gravity; and an associating process for correlating the position data with the calibration data in a look-up table.

9. A device for imaging by means of an image pick-up device which is attached to a gravity-sensitive supporting construction, the device comprising:

means for determining the direction of the force of gravity relative to the supporting construction;

an arithmetic and storage unit for determining position data of the supporting construction, related to the direction of the force of gravity, in order to compare this position data with the position data stored in a look-up table, to read out calibration data stored at position data in the look-up table which corresponds at least essentially to the determined position data, as well as to remove distortions from the acquired image of the object to be examined or to distort the image of an instrument, introduced into the object to be examined, by way of the read out and possibly interpolated calibration data; and a display unit for displaying the distortion-corrected image of the object to be examined or for displaying the distorted image of the object to be examined in which the distorted image of the instrument is reproduced.

10. An X-ray system comprising:

an x-ray source;

an image intensifier;

a supporting construction upon which the x-ray source and the image intensifier is mounted;

means for determining the direction of the force of gravity relative to a selected position of the supporting construction; and an arithmetic and storage unit for determining position data, related to the direction of the force of gravity, for a plurality of selected positions of the supporting construction and for forming and storing a look-up table whereby the position data is associated with the respective calibration data which is suitable for the removal of image distortions caused by mechanical deformations in these positions.

* * * * *